(12) United States Patent
Shonohara (10) Patent No.: US 7,157,921 B2
(45) Date of Patent: Jan. 2, 2007

(54) TFT ARRAY INSPECTION APPARATUS

(75) Inventor: Makoto Shonohara, Hadano (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/825,334

(22) Filed: Apr. 16, 2004

(65) Prior Publication Data

US 2004/0223140 A1 Nov. 11, 2004

(30) Foreign Application Priority Data

May 9, 2003 (JP) .............................. 2003-131246

(51) Int. Cl.
*G01R 31/02* (2006.01)
*G01R 31/26* (2006.01)

(52) U.S. Cl. ....................... 324/751; 324/770

(58) Field of Classification Search ........ 324/750–753, 324/770, 501; 250/306–607
See application file for complete search history.

(56) References Cited

U.S. PATENT DOCUMENTS

| | | | | |
|---|---|---|---|---|
| 4,906,922 A | * | 3/1990 | Takahashi et al. | .......... 324/753 |
| 5,432,461 A | * | 7/1995 | Henley | .......... 324/770 |
| 5,982,190 A | * | 11/1999 | Toro-Lira | .......... 324/770 |
| 6,765,203 B1 | * | 7/2004 | Abel | .......... 250/310 |
| 6,873,175 B1 | * | 3/2005 | Toro-Lira et al. | .......... 324/770 |

* cited by examiner

*Primary Examiner*—Minh N. Tang
(74) *Attorney, Agent, or Firm*—Manabu Kanesaka

(57) ABSTRACT

A TFT array inspection apparatus inspects a TFT array by irradiating an electron beam on a TFT substrate to obtain potential information. The TFT array inspection apparatus includes a scanning device for scanning the TFT substrate with an electron beam; a defect detecting device for detecting a defective site on the TFT substrate from a scanning signal of the TFT substrate; an irradiating device for irradiating the electron beam on the detected defective site; and a defect analyzing device. The defect analyzing device analyzes at least a type and/or an extent of the defect of the defective site based on a waveform change of a secondary electron signal detected through the electron beam irradiation and a driving state of the TFT.

6 Claims, 10 Drawing Sheets

TFT ARRAY INSPECTION APPARATUS

BACKGROUND OF THE INVENTION AND RELATED ART STATEMENT

The present invention relates to a TFT (thin film transistor) array inspection apparatus for inspecting a thin film transistor array substrate used for a liquid crystal display, an organic electro-luminescent display and the like.

As a TFT substrate inspection apparatus, there has been known an apparatus for inspecting a defect in which a probe of an oscilloscope contacts a TFT substrate to obtain a signal waveform. In such an apparatus, it is necessary to mechanically move the probe to contact the TFT substrate, thereby taking a long time for the inspection. To solve the problem, there has been known an apparatus for performing a GO/NG inspection in which a defective site on a TFT substrate is optically extracted and a probe contacts the defective site obtained through the GO/NG inspection to thereby inspect the TFT substrate.

However, even in an apparatus for performing the GO/NG inspection, after a defective site is detected, the probe needs to contact the TFT substrate. As described above, in the TFT substrate inspection using the probe, a tip of the probe needs to directly contact a surface of the TFT substrate, thereby causing a risk of damaging the TFT substrate. In addition to the problem of damaging the substrate, it is mechanically difficult to position the probe at a specific pixel on the TFT substrate. Especially when the TFT substrate has a large size, since a stage for supporting the TFT substrate has a limited positioning accuracy, it is difficult to accurately position the probe. Also, since the probe mechanically contacts the TFT substrate, it is difficult to secure reliable contact, thereby making it difficult to distinguish a loose contact of the probe from the defect.

In contrast with the TFT substrate inspection through the probe contact, there has been proposed a non-contact TFT substrate inspection apparatus without using the probe. Such a TFT substrate inspection apparatus inspects the TFT array through irradiating an electron beam on the TFT array and detecting a discharged secondary electron to inspect the TFT array with a voltage contrast phenomenon. In the voltage contrast phenomenon, when an electron beam is irradiated on a sample, a secondary electron is discharged from the sample surface. An energy distribution of the secondary electron is shifted in proportion to a voltage applied to the sample. A voltage of the TFT substrate is measured to detect a change in the secondary electron, and it is determined whether the measured voltage is a predetermined voltage to inspect the TFT substrate. Such a TFT substrate inspection apparatus as described above has been disclosed in, for example, Japanese Patent Publication (Kokai) No. 2000-3142, or Japanese Patent Publication (Kokai) No. 11-265678.

In the conventional TFT substrate inspection apparatus including the inspection apparatus using the probe or the non-contact inspection apparatus using the electron beam, there has been a problem that a long period of time is required in order to carry out a detailed defect inspection at a specific site of the TFT substrate.

In the inspection apparatus using the probe, the probe is moved relative to the TFT substrate and contacts a pixel at the moved position for the defect inspection repeatedly. Therefore, a long inspecting time is required to inspect the whole surface of the TFT substrate.

In the inspection apparatus using the electron beam, the electron beam is irradiated at an extremely small region relative to the TFT substrate. Accordingly, it is necessary to irradiate the electron beam at positions sequentially relative to the TFT substrate to inspect a defect over the entire surface of the TFT substrate as in the inspection using the probe, thereby taking a long inspecting time.

In the conventional inspection apparatuses, even if the TFT substrate contains a few number of sites to be inspected in detail and almost all sites do not require the inspection, it is still necessary to carry out the same defect inspection over the whole surface of the TFT substrate. Thus, it is inevitable to take a long period of time for the inspection. Especially when the TFT substrate has a large size, the problem becomes serious.

In view of the above problems, it is an object of the invention to provide a TFT array inspection apparatus, wherein a time for a detailed defect inspection of a specific site on a TFT substrate is shortened.

Further objects and advantages of the invention will be apparent from the following description of the invention.

SUMMARY OF THE INVENTION

According to the present invention, a TFT array inspection apparatus inspects only a defective site on the TFT substrate and not a whole surface of the TFT substrate, thereby reducing an inspection time required for a detailed defect inspection of the TFT substrate.

According to a first aspect of the invention, a TFT array inspection apparatus inspects a TFT array by irradiating an electron beam on a TFT substrate to obtain potential information. The TFT array inspection apparatus includes an irradiating device for irradiating the electron beam on a specific pixel and/or a specific site in a specific region on the TFT substrate; and a defect analyzing device for analyzing a defect of the specific pixel and/or the specific site in the specific region based on a waveform change of a detected secondary electron signal and a driving state of TFT.

In the first aspect of the present invention, the irradiating device irradiates the electron beam at the specific pixel or the specific site in the specific region on the TFT substrate, and does not irradiate the electron beam at other portions of the TFT substrate. The defect analyzing device carries out a detailed defect inspection only for the specific site where the irradiating device irradiates the electron beam. Accordingly, it is possible to perform the defect inspection only for the defective site without carrying out the defect inspection over the whole surface of the TFT substrate, thereby reducing an inspecting time.

According to a second aspect of the invention, a TFT array inspection apparatus inspects a TFT array by irradiating an electron beam on a TFT substrate to obtain potential information. The TFT array inspection apparatus includes a scanning device for scanning the TFT substrate with an electron beam; a defect detecting device for detecting a defective site on the TFT substrate from a scanning signal of the TFT substrate; an irradiating device for irradiating the electron beam on the detected defective site; and a defect analyzing device for analyzing at least a type and/or an extent of the defect of the defective site based on a waveform change of a secondary electron signal detected through the electron beam irradiation and a driving state of the TFT.

In the second aspect of the present invention, the scanning device scans the whole TFT substrate with the electron beam, and the defect detecting device extracts the defective site from the whole TFT substrate based on the detected signal from the scanning device. On the other hand, the irradiating device irradiates the electron beam only at the detected site on the TFT substrate, and the defect analyzing device analyzes the detective site in detail to determine a type and an extent of the defect.

Although the scanning device and the defect detecting device extract the defective site over the whole TFT substrate, the process is only to determine whether the defect is exist or not. The irradiating device and the defect analyzing device inspect the defect only at the defective site on the TFT substrate, so that the processing time of both devices becomes shorter than that required in a case where the defect inspection is carried out over the entire TFT substrate.

In the second aspect of the invention, an operation of the scanning device is shifted to that of the irradiating device in synchronism with shifting of operations of the defect detecting device and the defect analyzing device. Therefore, it is possible to continuously extract the defective site and perform the defect inspection with respect to the extracted defective site.

In the second aspect of the invention, the defective site may include a defective pixel and/or a defective region including the defective pixel on the TFT substrate. The defective region covers a wide area of pixels including the defective pixels, and may include all defective pixels or a combination of normal pixels and defective pixels. In the irradiating device, it is possible to select an irradiation region between only at the defective pixel or the defective region by adjusting the irradiation area. Also, a size of the defective region can be selected.

BRIEF DESCRIPTION OF THE DRAWINGS

FIGS. 1(a) to 1(d) are schematic views for explaining a defect inspection of a TFT array detecting apparatus according to an embodiment of the present invention, wherein FIGS. 1(a) and 1(b) are views showing a case of inspecting a defective pixel on a TFT substrate, and FIGS. 1(c) and 1(d) are views showing a case of inspecting a defective region on the TFT substrate;

FIGS. 2(a) to 2(c) are schematic charts showing signals for a defect analysis, wherein FIG. 2(a) shows a gate signal of a TFT substrate array, FIG. 2(b) shows a source signal thereof, and FIG. 2(c) shows a detected signal obtained from a secondary electron;

DETAILED DESCRIPTION OF PREFERRED EMBODIMENTS

Figures 1A, 1B:
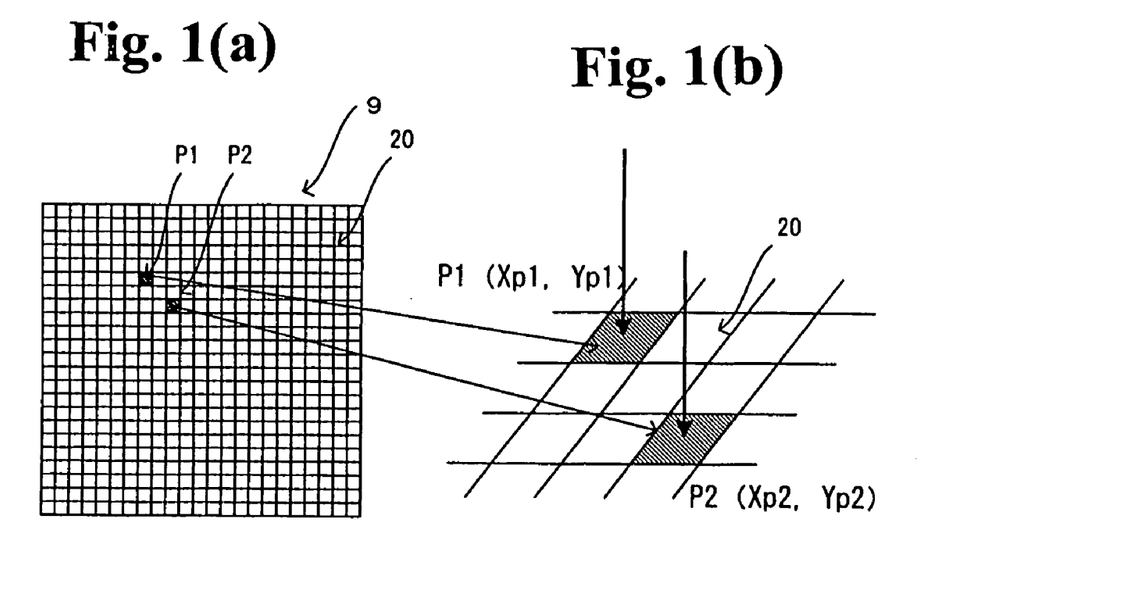
Figure 1C:
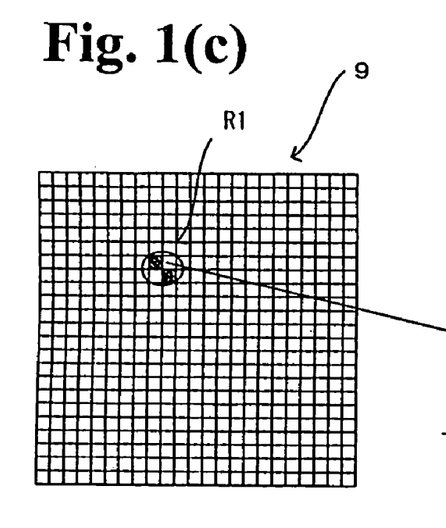
Figure 1D:
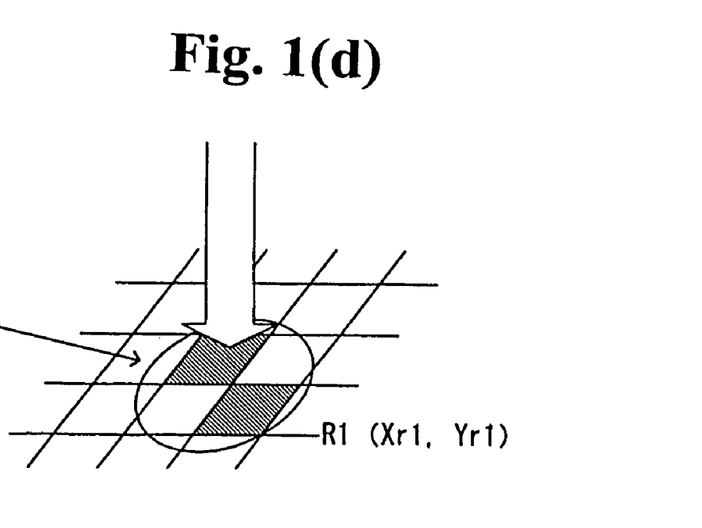

Hereunder, embodiments of the present invention will be described in detail with reference to the accompanying-drawings. FIGS. 1(a) to 1(d) are schematic views for explaining a defect inspection of a TFT array detecting apparatus according to an embodiment of the present invention. FIGS. 1(a) and 1(b) are views showing a case of inspecting a defective pixel on a TFT substrate, and FIGS. 1(c) and 1(d) are views showing a case of inspecting a defective region on the TFT substrate.

A TFT substrate 9 is formed of a plurality of pixels 20 formed in an array pattern. In FIGS. 1(a) and 1(c), first, an inspection called a GO/NG inspection is carried out over the entire TFT substrate 9 to determine which pixels have defects. In the GO/NG inspection, it is theoretically possible to carry out a detailed real-time analysis of the defects. However, it is necessary to process a large amount of data at a high speed. Therefore, the process requires a long period of time, and is not practical.

In the embodiment of the present invention, an electron beam is irradiated on a pixel or a region detected as a defective site during the GO/NG inspection, so that a detailed defect analysis is carried out for only a small specific site, thereby shortening the processing time.

In FIG. 1(b), an electron beam is irradiated at a pixel P1 and a pixel P2 detected as defective during the GO/NG inspection, and a secondary electron is detected with respect to the pixels to thereby analyze the defects. The electron beam is irradiated at the pixels using coordinate data ($X_{p1}$, $Y_{p1}$), ($X_{p2}$, $Y_{p2}$) of the defective pixels detected during the GO/NG inspection.

In FIG. 1(c), an electron beam is irradiated on a defective region R1 detected as defective during the GO/NG inspection, and a secondary electron discharged from the irradiated region is detected to thereby analyze the defect. The electron beam is irradiated on the defective region using coordinate data ($X_{r1}$, $Y_{r1}$) of the defective region detected during the GO/NG inspection.

Figure 2A:
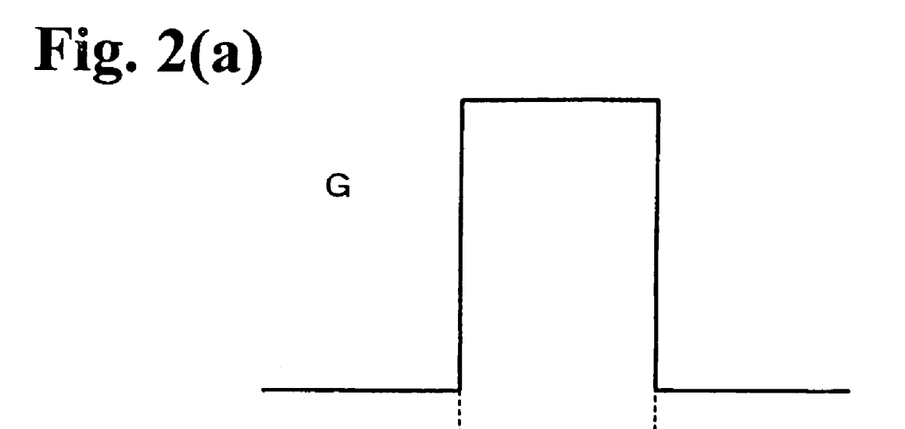
Figure 2B:
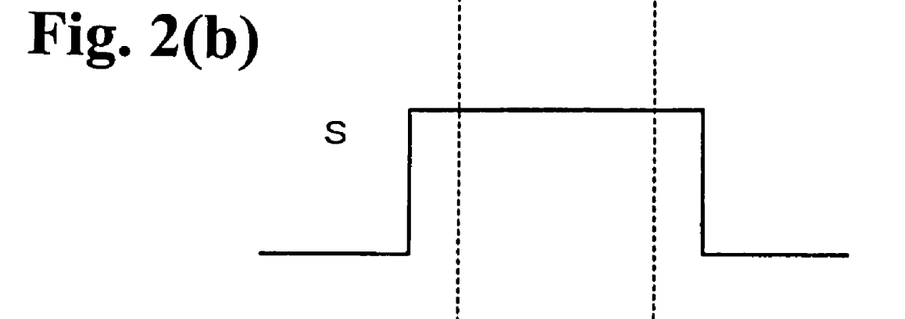
Figure 2C:
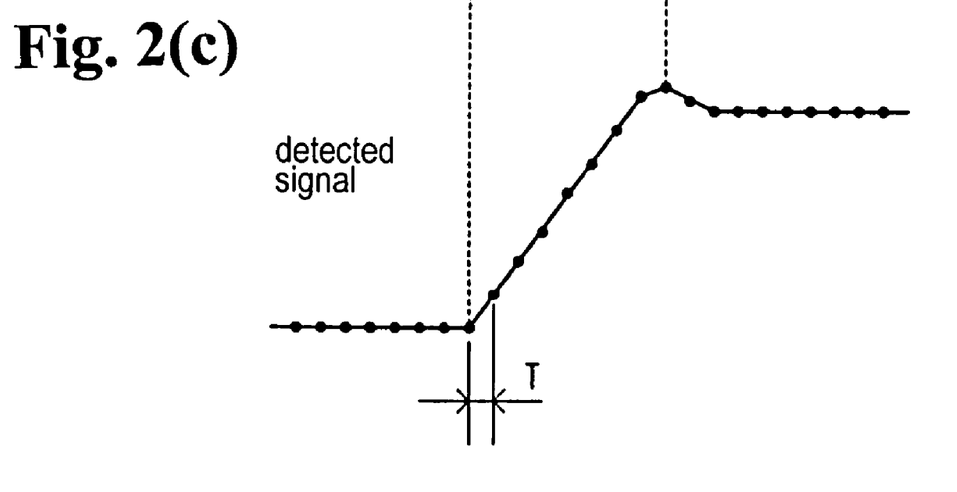

FIGS. 2(a) to 2(c) are schematic charts showing signals for the defect analysis. FIG. 2(a) shows a gate signal of a TFT substrate array, FIG. 2(b) shows a source signal thereof, and FIG. 2(c) shows a detected signal obtained from a secondary electron. Incidentally, the detected signals are detected with an interval of a sampling time T.

A detected signal obtained from the secondary electron exhibits a specific pattern according to a combination of, for example, a gate signal and a source signal. In FIG. 2(c), the detected signal starts increasing when both gate signal and source signal are turned on. The detected signal starts decreasing when the gate signal is turned off, and holds a voltage at a time when the source signal is turned off.

At this time, in a case that there is a defect such as a short circuit, leak, and opening on the TFT substrate, the detected signal pattern is changed. Accordingly, it is possible to analyze a type and extent of the defect on the TFT substrate through the change in the pattern of the voltage applied to the TFT substrate and in the pattern of the detected signal.

Figure 3:
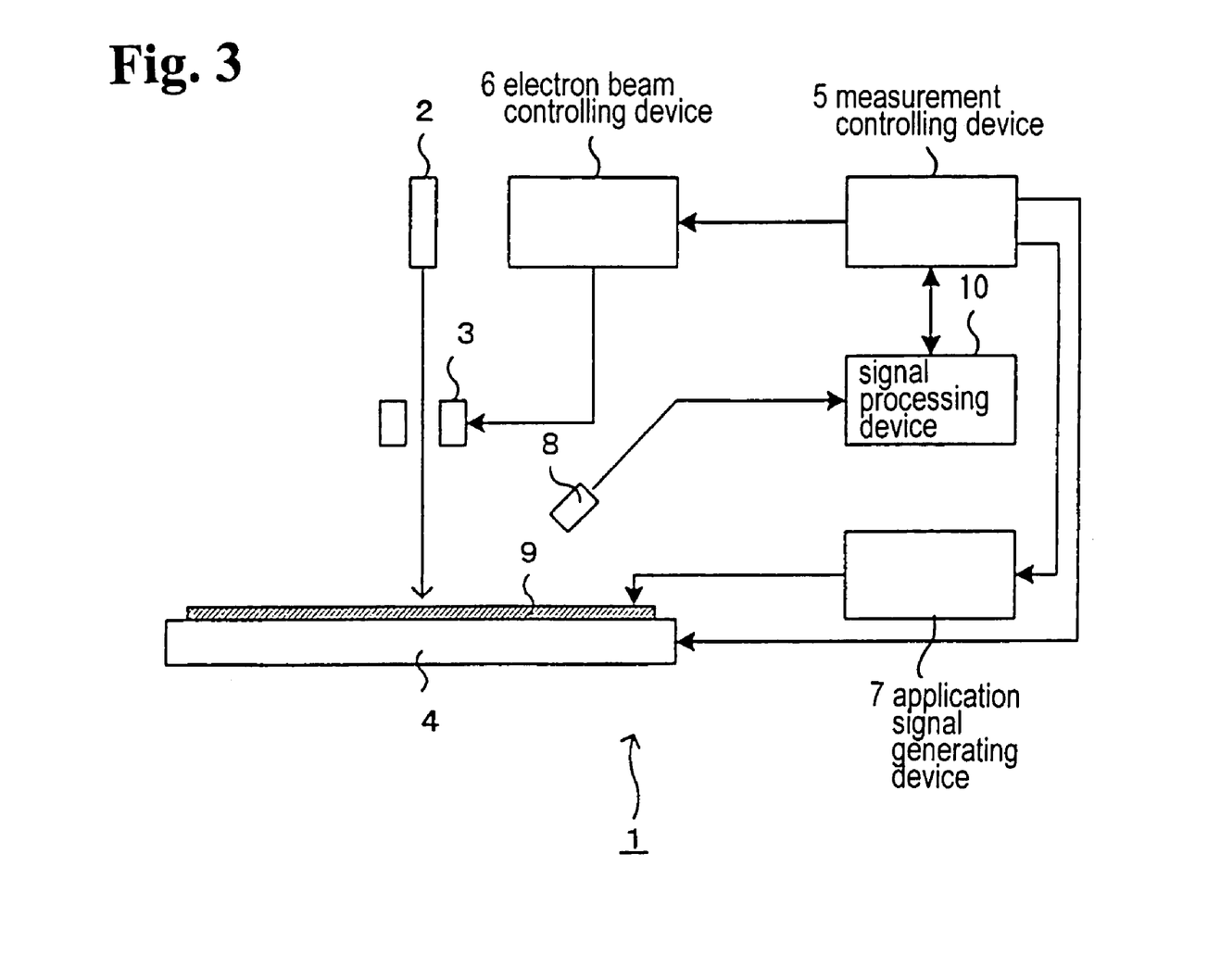
FIG. 3 is a block diagram for explaining a structure of the TFT array inspection apparatus according to the embodiment of the present invention.

FIG. 3 is a block diagram for explaining a structure of the TFT array inspection apparatus according to the embodiment of the invention. In the TFT array inspection apparatus 1, an electron gun 2 irradiates an electron beam on a TFT substrate 9 held on a stage 4. A detector 8 detects a secondary electron discharged from the TFT substrate 9, so that a change in the secondary electron is detected to measure a voltage of the TFT substrate. It is determined whether the measured voltage is a predetermined voltage for inspecting the TFT substrate.

The TFT array inspection apparatus 1 includes an electron beam controlling device 6 for controlling irradiation of the electron beam on the TFT substrate 9 together with the stage 4. With this control, the entire TFT substrate 9 is scanned or a specific site of the TFT substrate 9 is irradiated. At this time, a predetermined inspection signal is inputted to the TFT substrate 9 from an application signal generating device 7, so that a predetermined voltage pattern is applied to the array on the TFT substrate. A measurement controlling device 5 controls the electron beam controlling device 6 and the stage 4 to scan the entire TFT substrate or irradiate at a specific site thereof, and the application signal generating device 7 to generate the inspecting signal.

The TFT array inspection apparatus 1 includes a signal processing device 10 for carrying out a defect inspection for detecting a defective site through the scanning of the entire TFT substrate, and a defect analysis for analyzing the defective site in detail. The signal processing device 10 stores positional information of a defective site detected during the defect inspection, and reads out the positional information of the defective site during the defective analysis to irradiate the electron beam at the defective site, so that the defect is analyzed by the obtained secondary electron.

Figure 4:
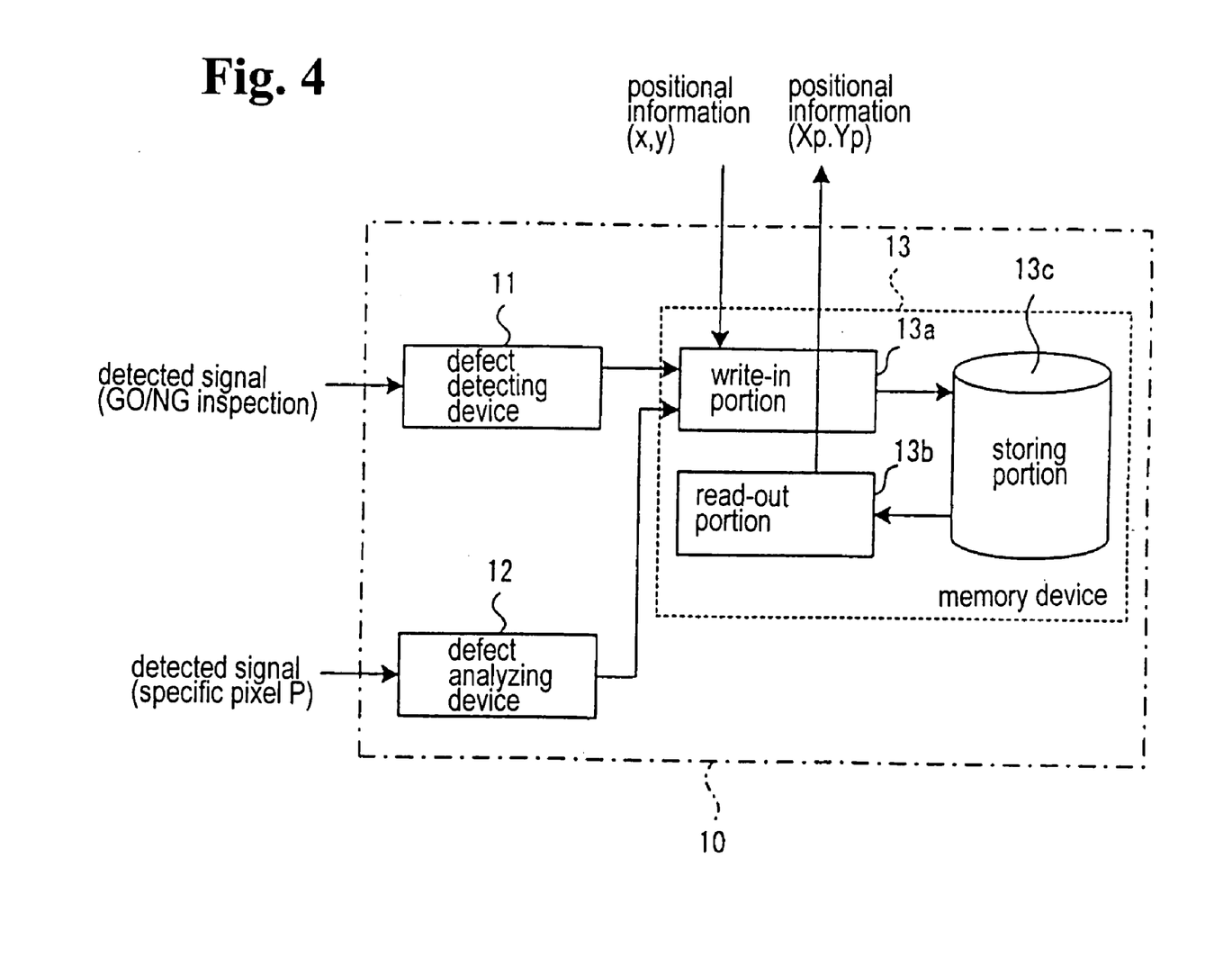
FIG. 4 is a block diagram for explaining a structure of a signal processing device according to the invention.

FIG. 4 is a block diagram for explaining a structure of the signal processing device. The signal processing device 10 includes two devices for processing the detected signal, i.e. a defect detecting device 11 for detecting the defective site based on the scan signal of the entire TFT substrate, and a defect analyzing device 12 for analyzing the defect of the defective site based on the detected signal obtained by irradiating the electron beam at the specific site. A memory device 13 stores positional information of the defective site detected by the defect detecting device 11 and an analysis result analyzed by the defect analyzing device 12. When the electron beam is irradiated at the defective site, the positional information $(X_p, Y_p)$ of the defective site stored in the memory device 13 is read out.

The memory device 13 includes a storing portion 13c; a write-in portion 13a for storing data in the storing portion 13c; and a read-out portion 13b for reading out the data stored in the storing portion 13c. When the defect detecting device 11 detects a defect, the write-in portion 13a obtains positional information (x, y) of the defective pixel or the defective region from the measurement controlling device 5 and the like, and writes-the data in the storing portion 13c as the positional information $(X_p, Y_p)$ of the defective site. When the defect analysis is carried out, the read-out portion 13b reads out the positional information $(X_p, Y_p)$ of the defective site from the storing portion 13c, and the electron beam is irradiated at the defective site based on the positional information.

Figure 5:
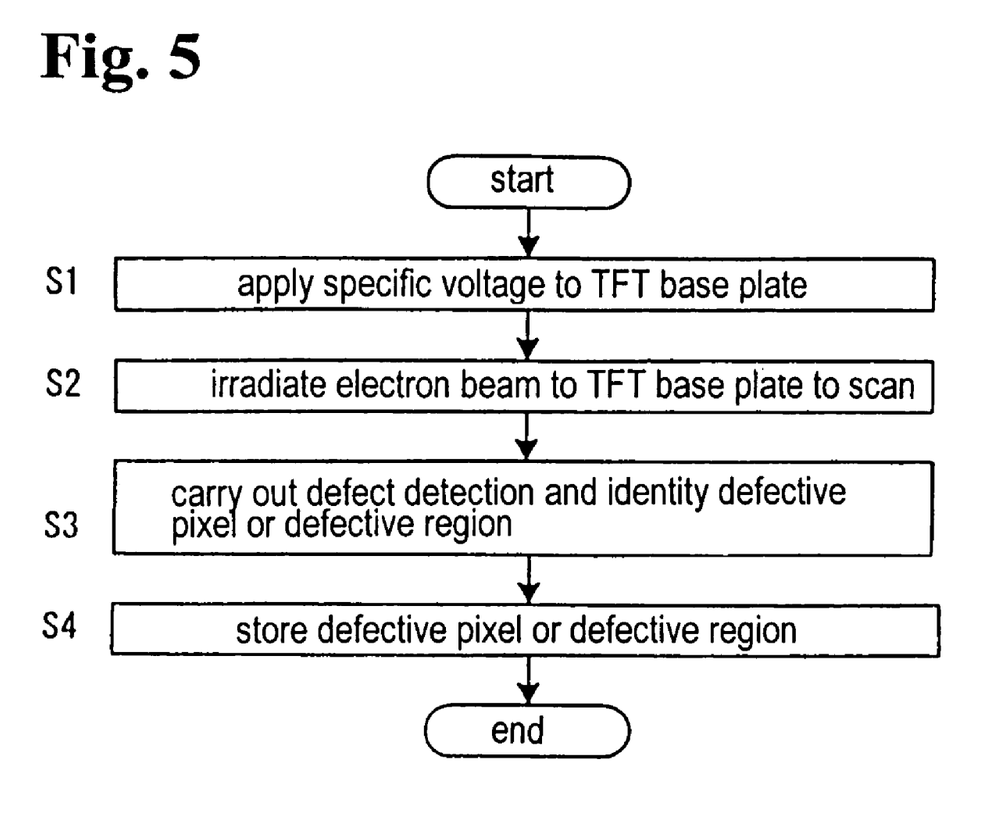
FIG. 5 is a flow chart for explaining a defect detecting process of the TFT array inspection apparatus according to the embodiment of the present invention.
Figure 6:
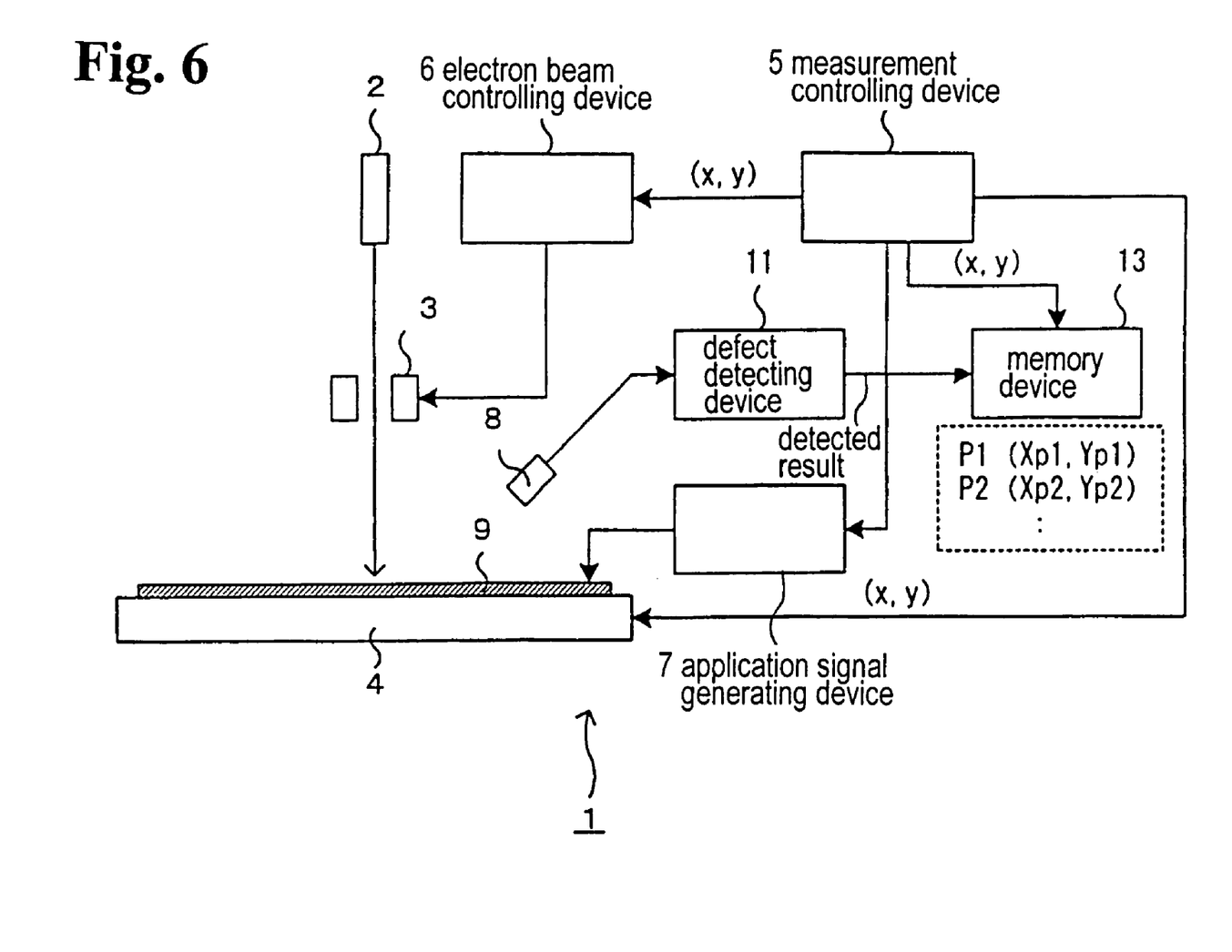
FIG. 6 is a block diagram for explaining the defect detecting process of the TFT array inspection apparatus according to another embodiment of the present invention.

Hereunder, a process of the defect detection of the TFT array inspection apparatus according to the embodiment of the invention will be explained with reference to a block diagram shown in FIG. 6 and a flow chart shown in FIG. 5. A process of the defect analysis by the TFT array inspection apparatus according to the embodiment of the invention will be explained with reference to a block diagram shown in FIG. 8 and a flow chart shown in FIG. 7.

First, the defect detection is carried out. An application signal generating device 7 applies a predetermined voltage to the TFT substrate 9 placed on the stage 4 (Step S1) and the scanning is carried out by irradiating the electron beam on the TFT substrate 9. The scanning is carried out through control of the electron beam controlling device 6 and the stage 4 by the measurement controlling device 5 (Step S2). A detector 8 detects the secondary electron discharged from the TFT substrate 9 during the scanning of the TFT substrate 9. The defect detecting device 11 carries out the defect detection based on the detected signal of the detector 8 to identify a defective pixel or a defective region (Step S3). The memory device 13 stores the positional data $(X_{p1}, Y_{p1})$, $(X_{p2}, Y_{p2})$, . . . ) of the defective pixels or the defective regions based on the detected results (Step S4).

Figure 7:
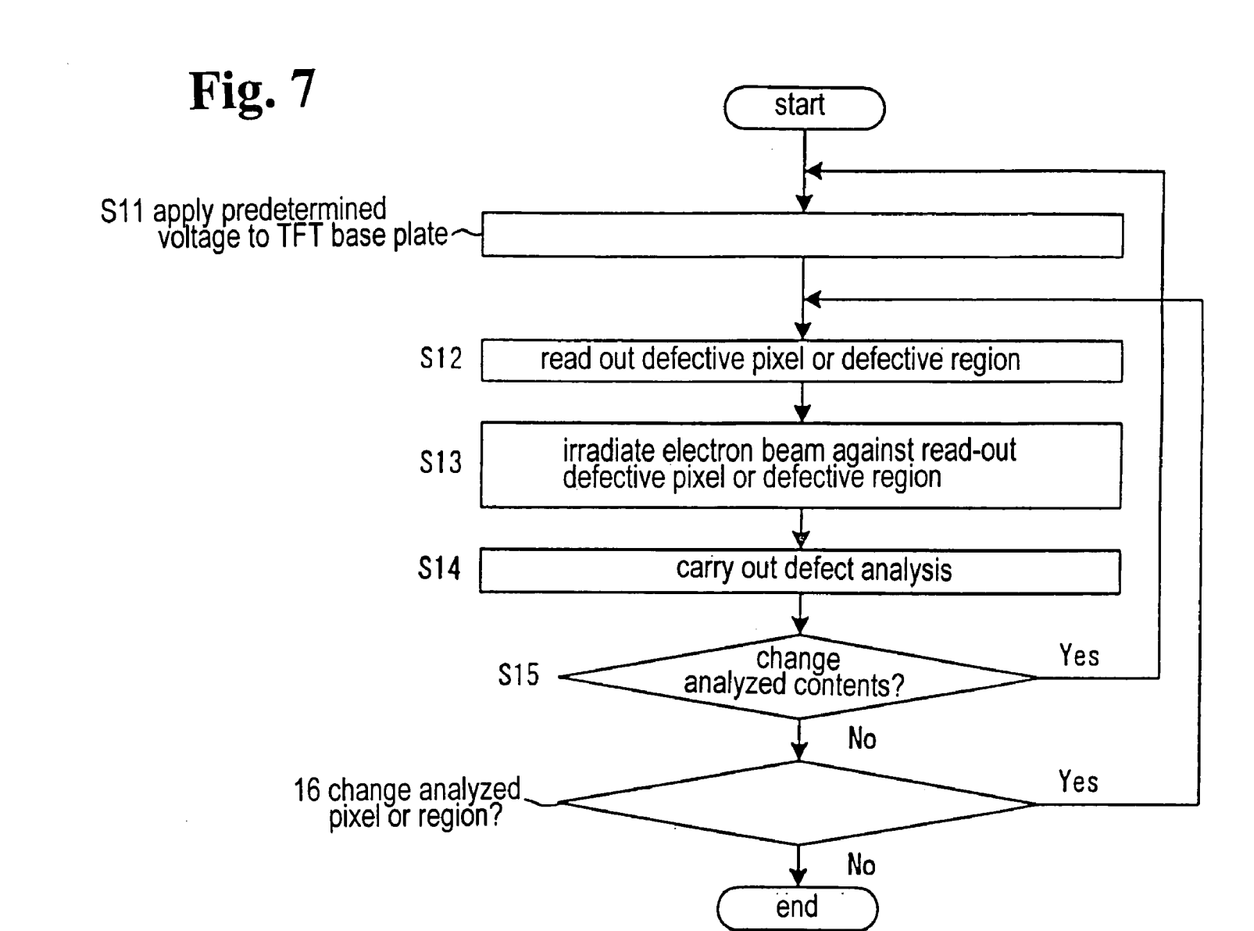
FIG. 7 is a flow chart for explaining a defect analyzing process of the TFT array inspection apparatus according to the embodiment of the present invention.
Figure 8:
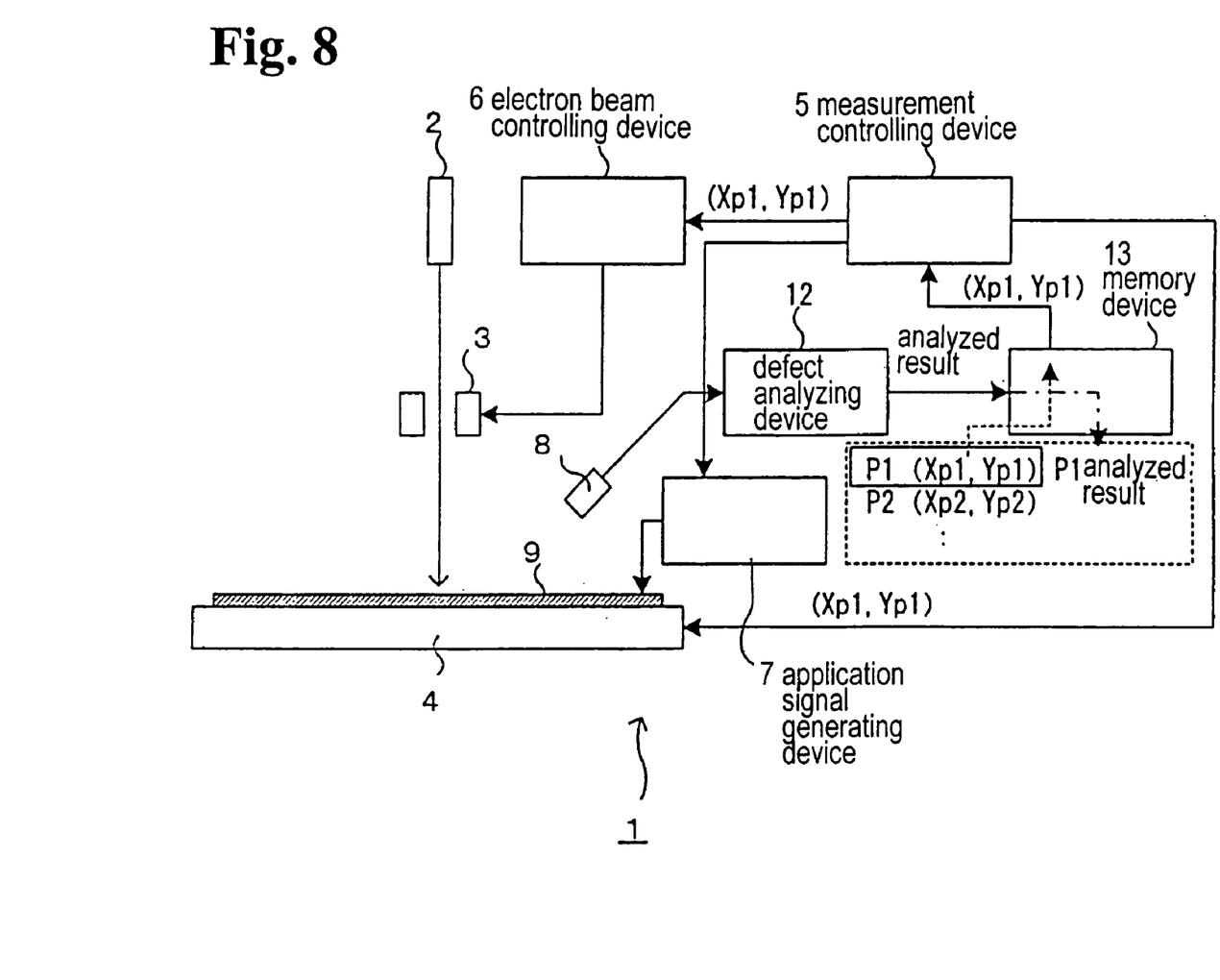
FIG. 8 is a block diagram for explaining the defect analyzing process of the TFT array inspection apparatus according to the embodiment of the present invention.

Next, the defect analysis is carried out. In the defect analysis, the scanning of the electron beam on the entire TFT substrate is shifted to the irradiation of the electron beam only on a specific site. The signal processing is shifted from the defect detection to the defect analysis. Both shifts can be carried out at the same time, so that it is possible to inspect a plurality of TFT substrates continuously.

The application signal generating device 7 applies a predetermined voltage to the TFT substrate 9 for the defect detection. The voltage has a voltage pattern according to content of the defect analysis (Step S11). The positional information of the defective pixel or the defective region is read out from the memory device 13 (Step S12), and the electron beam is irradiated at the defective pixel or the defective region based on the positional information. The electron beam irradiation is carried out by taking the positional information into the measurement controlling device 5 from the memory device 13 to control the electron beam control device 6 and the stage 4. The electron beam is irradiated locally, and the electron beam has a diameter smaller than that in the scanning process according to the pixel or the region (Step S13).

The detector 8 detects the secondary electron discharged from the TFT substrate. The defect analyzing device 12 carries out a defect analysis based on the detected signal of the detector 8 and the applied voltage pattern. The analyzed result is stored in the memory device 13 (Step S14).

When the content of the defect analysis is changed, the voltage pattern applied to the TFT substrate is changed and Steps S11 to S14 are repeated (Step S15). When the defect analysis is carried out with respect to another defective site, the positional information of the defective site is read out from the memory device 13, and Steps S12 to S15 are repeated (Step S16).

Figure 9:
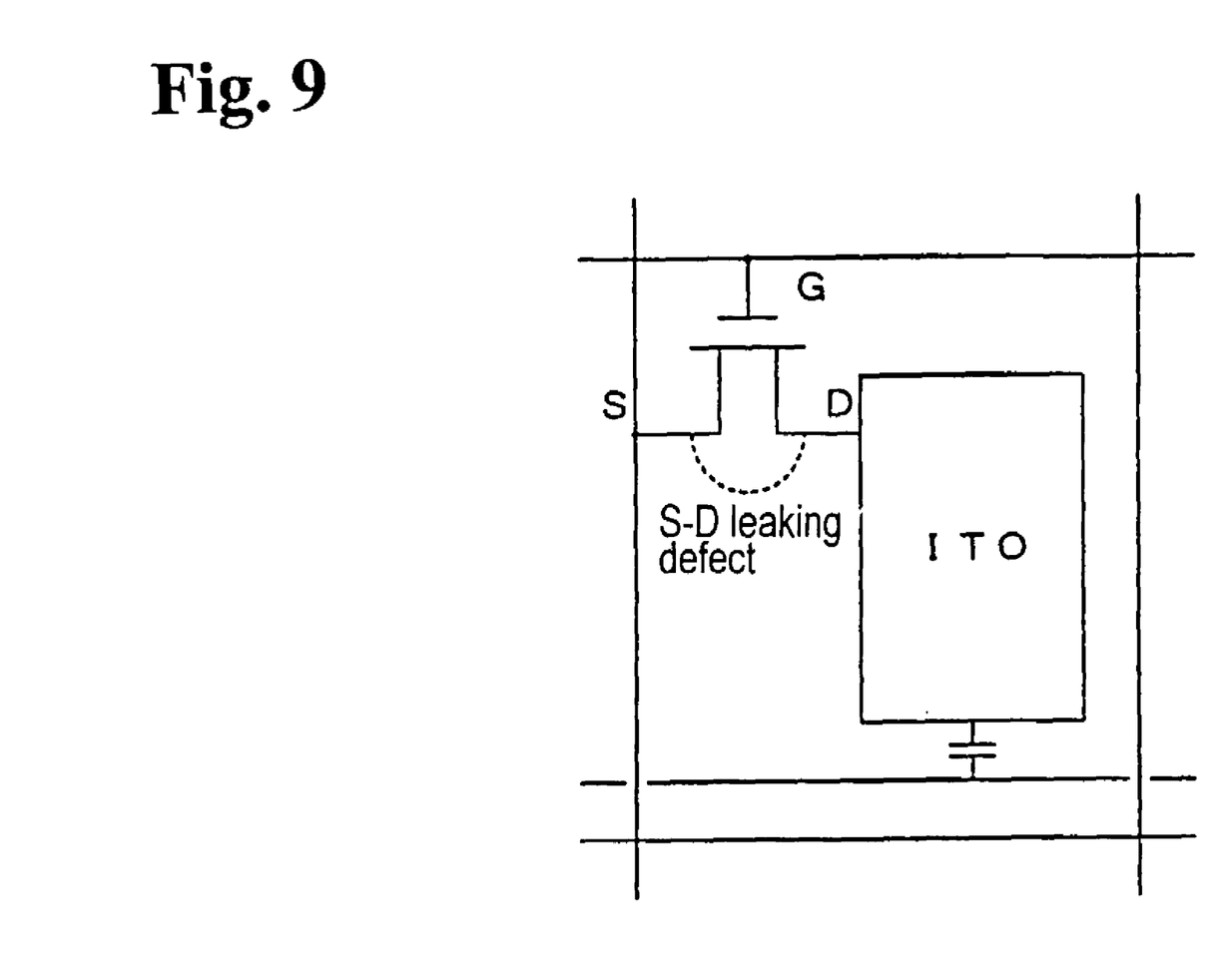
FIG. 9 is a schematic view of a pixel on the TFT substrate for explaining the defect analysis by the TFT array inspection apparatus according to the embodiment of the present invention.
Figure 10A:
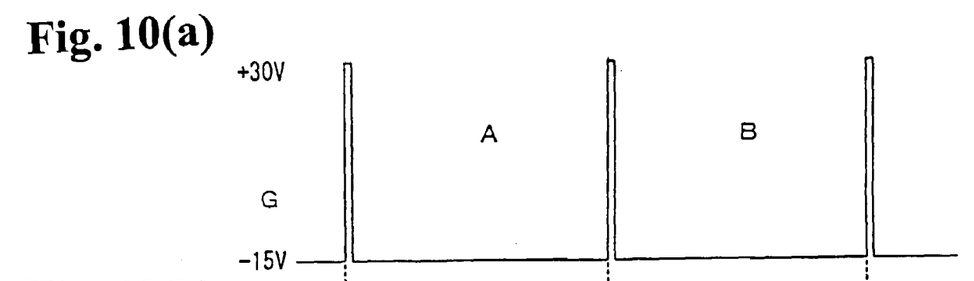
FIGS. 10(a) to 10(c) are schematic charts showing pixel signals of the TFT substrate for explaining the defect analysis by the TFT array inspection apparatus according to the embodiment of the present invention.
Figure 10B:
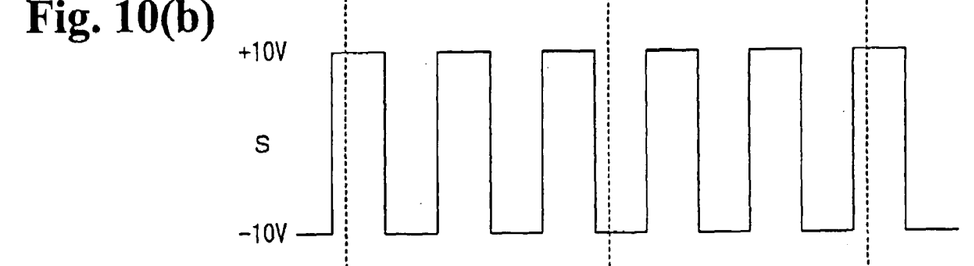
Figure 10C:
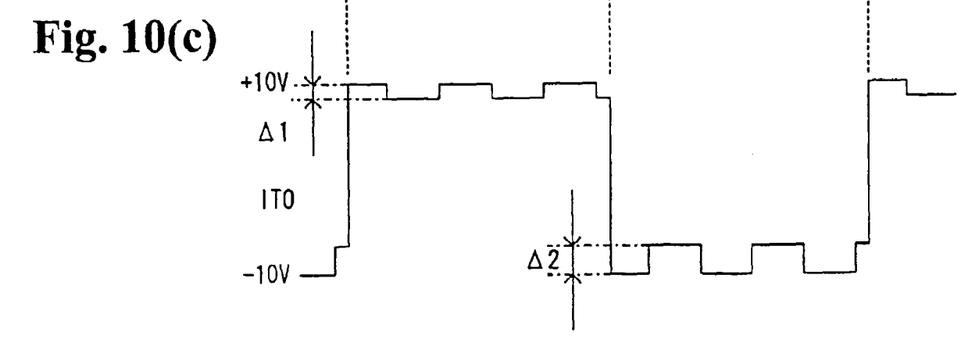

FIG. 9 is a schematic view of a pixel on the TFT substrate, and FIGS. 10(a) to 10(c) are schematic charts showing pixel signals of the TFT substrate for explaining the defect analysis. In FIG. 9, a gate G and a source S of the pixel are connected to a gate line and a source line, respectively, and a drain D is connected to an ITO portion (transparent conductive film substrate). When the electron beam is irradiated at the pixel, the secondary electron corresponding to a voltage applied to the ITO portion is discharged. It is possible to determine a type and extent of the defect of the pixel from a change in a detected signal of the secondary electron and a state of the applied voltage.

In this example, an analysis of a leaking defect between the source S and the drain D will be explained. In FIG. 10(a), a portion A represents a state that the gate is on or a potential of the ITO portion is +10 V, and a portion B represents a state that the gate is off, or the potential of the ITO portion is −10 V. In a case that there is no leaking defect between the source S and the drain D, when the voltage of the source signal is changed between positive and negative while the gate is on or off, a change in the voltage at the ITO portion is within a predetermined small range. On the contrary, in a case that there is a leaking defect between the source S and the drain D, when the voltage of the source signal changes between positive and negative, the voltage at the ITO portion changes. The voltage changes by Δ1 when the gate is in an on state, and the voltage changes by Δ2 when the gate is in an off state, thereby causing a difference in the voltage variation. The difference (Δ2−Δ1) in the voltage variation corresponds to the extent of the leaking defect.

Accordingly, it is possible to determine the extent of the leaking defect by obtaining the difference (Δ2−Δ1) in the voltage variation. Incidentally, in the embodiment, after the position of the defective site is detected through the scanning of the TFT substrate, the detailed defect inspection of the defective site is carried out through the irradiation of the electron beam only at the defective site. It is also possible to use positional information of the defective site obtained by other inspection apparatus in advance. Incidentally, it is possible to defect other types of defects such as a short circuit and an opening, and to determine an extent of the defects by changing the voltage pattern to be applied.

As described hereinabove, according to the embodiments of the present invention, it is possible to perform the detailed defect inspection of the specific site on the TFT substrate in a short period of time.

While the invention has been explained with reference to the specific embodiments of the invention, the explanation is illustrative and the invention is limited only by the appended claims.

What is claimed is:

1. A TFT array inspection apparatus for inspecting a TFT array, comprising:
    irradiating means for irradiating an electron beam on the TFT array including a specific pixel and a specific site on a TFT substrate to obtain a secondary electron signal,
    scanning means for scanning the electron beam on the TFT substrate to obtain a scanning signal,
    defect detecting means for detecting a defective site on the TFT substrate according to the scanning signal,
    defect analyzing means for analyzing at least one of a type and an extent of a defect in the defective site based on a change in a waveform of the secondary electron signal and a driving state of the TFT array, and
    a memory electrically connected to the defect detecting means and the defect analyzing means so that the defective site on the TFT substrate is memorized in the memory when the defect detecting means detects the defective site, and the defective site in the memory is provided to eject electron beam from the irradiating means when the defect analyzing means is operated,
    wherein said defect analyzing means analyzes the defective site in detail after the defect detecting means finds the defective site by scanning the entire TFT array.

2. A TFT array inspection apparatus according to claim 1, further comprising switching means for switching operations between the scanning means and the irradiating means and operations between the defect detecting means and the defect analyzing means, said switching means synchronously switching between the scanning means and the irradiating means and between the defect detecting means and the defect analyzing means.

3. A TFT array inspection apparatus according to claim 1, wherein said defect detecting means detects the defective site including a defective region having a defective pixel on the TFT substrate.

4. A TFT array inspection apparatus according to claim 1, wherein said irradiating means is an electron gun for irradiating the electron beam on the TFT substrate so that a secondary electron is discharged from the TFT substrate.

5. A TFT array inspection apparatus according to claim 4, further comprising detecting means located above the TFT substrate for detecting the secondary electron discharged from the TFT substrate to obtain the secondary electron signal, and signal generating means electrically connected to the TFT substrate for applying an inspection signal to the TFT substrate, said defect analyzing means being electrically connected to the detecting means and the signal generating means for analyzing the defective site based on the secondary electron signal and the inspection signal.

6. A TFT array inspection apparatus according to claim 5, further comprising a stage for placing the TFT substrate capable of moving the TFT substrate horizontally.

* * * * *

UNITED STATES PATENT AND TRADEMARK OFFICE
CERTIFICATE OF CORRECTION

PATENT NO. : 7,157,921 B2 Page 1 of 1
APPLICATION NO. : 10/825334
DATED : January 2, 2007
INVENTOR(S) : Makoto Shinohara It is certified that error appears in the above-identified patent and that said Letters Patent is hereby corrected as shown below:

Title page, item [75]
Change the inventor's name, "Makoto ~~Shonohara~~" to --Makoto <u>Shinohara</u>--.

Signed and Sealed this

Twentieth Day of March, 2007

JON W. DUDAS
*Director of the United States Patent and Trademark Office*